(12) United States Patent
Jin et al.

(10) Patent No.: US 6,987,087 B2
(45) Date of Patent: Jan. 17, 2006

(54) **PROTEASE OBTAINED FROM *VIBRIO METSCHNIKOVII* VARIANTS AND DETERGENT COMPOSITIONS COMPRISING THE ABOVE PROTEASE**

(75) Inventors: Ghee-Hong Jin, Seoul (KR);
Sung-Hoo Jhon, Seoul (KR);
Hyun-Hwan Lee, Youngin Si (KR);
Hyune-Mo Rho, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 373 days.

(21) Appl. No.: 10/228,040

(22) Filed: Aug. 27, 2002

(65) Prior Publication Data

US 2003/0096723 A1      May 22, 2003

(30) Foreign Application Priority Data

Oct. 19, 2001   (KR) ............................... 2001-64520

(51) Int. Cl.
*D06M 16/00*   (2006.01)
*C11D 3/00*    (2006.01)

(52) U.S. Cl. .................. 510/392; 435/219; 435/262; 435/264

(58) Field of Classification Search ............... 252/107; 510/392; 435/219, 262, 264
See application file for complete search history.

(56) References Cited

U.S. PATENT DOCUMENTS

| 4,463,113 A | 7/1984 | Nakahara et al. ........... 524/117 |
| 5,049,605 A | 9/1991 | Rekers ....................... 524/108 |
| 5,342,868 A | 8/1994 | Kimura et al. .............. 524/108 |

FOREIGN PATENT DOCUMENTS

| EP | 0335023 A1 | 3/1988 |
| WO | WO 88/03948 | 6/1988 |
| WO | WO 00/61769 | * 10/2000 |

* cited by examiner

*Primary Examiner*—Yocendra N. Gupta
*Assistant Examiner*—Preeti Kumar
(74) *Attorney, Agent, or Firm*—Mayer, Brown, Rowe & Maw LLP

(57) ABSTRACT

The present invention relates to a *Vibrio metscnikovii* variants, more particularly to a biochemical characteristics of protease which is obtained from *Vibrio metscnikovii* variant strains such as *Vibrio metschnikovii* KS1, *Vibrio metschnikovii* KS1 transformed with pDSBCm, *Vibrio metschnikovii* KS1 transformed with pSBCm and *Vibrio metschnikovii* RH530 N-4-8 strain, the mother strain of *Vibrio metschnikovii* and to a detergent composition including the protease.

5 Claims, 6 Drawing Sheets

PROTEASE OBTAINED FROM *VIBRIO METSCHNIKOVII* VARIANTS AND DETERGENT COMPOSITIONS COMPRISING THE ABOVE PROTEASE

TECHNICAL FIELD

The present invention relates to a *Vibrio metscnikovii* variants, more particularly to a biochemical characteristics of protease which is obtained from *Vibrio metscnikovii* variant strains such as *Vibrio metschnikovii* KS1, *Vibrio metschnikovii* KS1 transformed with pDSBCm, *Vibrio metschnikovii* KS1 transformed with pSBCm and *Vibrio metschnikovii* RH530 N-4-8 strain which is the mother strain of *Vibrio metschnikovii* and to a detergent compositions including the protease.

BACKGROUND ART

Up to now, an enzyme for a detergent has been exploited to remove contaminants by protein, fat, starch, etc. effectively with being added to a powder-type or liquid-type detergents. Recently, the amount of enzyme for a detergent increases to reinforce a declined washing power that is resulted from reducing amount of phosphate or toxic surfactant provoking a water pollution.

The enzyme for a detergent is classified into a protease, a lipase and a cellulase by decomposing cellulose which results in preventing decoloration of cloths. Presently, the protease among these is used as a main enzyme worldwidely. The enzymes mentioned above are also utilized as a detergent by being added into an automatic dish washer to reinforce a washing power.

Most of commercial proteases have been produced from *Bacillus* species for a few decades. Meanwhile, U.S. Pat. No. 5,472,865 has disclosed that the alkaline protease is produced from Fungi Imperfecti such as *Dendryphiella arenaria, Dendryphiella salina* or the like.

In addition, PCT International Patent WO 88/03947 has illustrated a method for preparing for producing a low temperature activating protease from *Nocardiopsis dassonvillei* belonging to *Actinomyces* sp. This research trend is because the conventional proteases derived from *Bacillus* sp. have similar characteristics in their enzymatic properties and have low activity in an organic solvent or at a low temperature.

The commercial proteases for a detergent manufactured by Novozyme company or Genencor company are proteases activating at a high temperature, which are suitable for a western washing pattern. On the contrary, it is unfavorable for a washing condition in Korea or South-eastern Asia due to using a low temperature water. Savinase, a low temperature activating protease manufactured by Novozyme company, and Maxacal, a similar type enzyme to Savinase manufactured by Genencor company, are also poorly activated at the temperature range of 20~25° C. actually.

In order to solve the above problems, the inventors of the present invention have patent applications such as Korean Patent Application No. 94-21000, No. 98-15971, No. 2000-41212, PCT International Patent WO 00/61769, etc. in which *Vibrio metschnikovii* RH530 N-4-8, a bacterial strain producing a low temperature activating protease, other superior variant strains of said bacteria, a method for preparing thereof, and a main enzymes thereof, especially about a biochemical characteristic, a genetic structure, a nucleotide sequence and the like were demonstrated.

DISCLOSURE OF THE INVENTION

In order to overcome the disadvantages of the conventional proteases for detergents, the object of the present invention is to elucidate a stability and biochemical characteristics of the protease for the use of a detergent obtained from *Vibrio metschnikovii* KS1, *Vibrio metschnikovii* KS1 transformed with pDSBCm, *Vibrio metschnikovii* KS1 transformed with pSBCm and *Vibrio metschnikovii* RH530 N-4-8 strain, the mother strain of the variants, which have been specified in Korean Patent Application No. 94-21000, 98-15971, 2000-41212 and PCT International Application WO 00/61769 applied by the inventors of the present invention.

Another object of the present invention is to elucidate a biochemical characteristic of the protease as to an improved washing power.

The other object of the present invention is to provide the detergent compositions including the protease mentioned above.

DETAILED DESCRIPTION OF THE INVENTION

Figure 1:
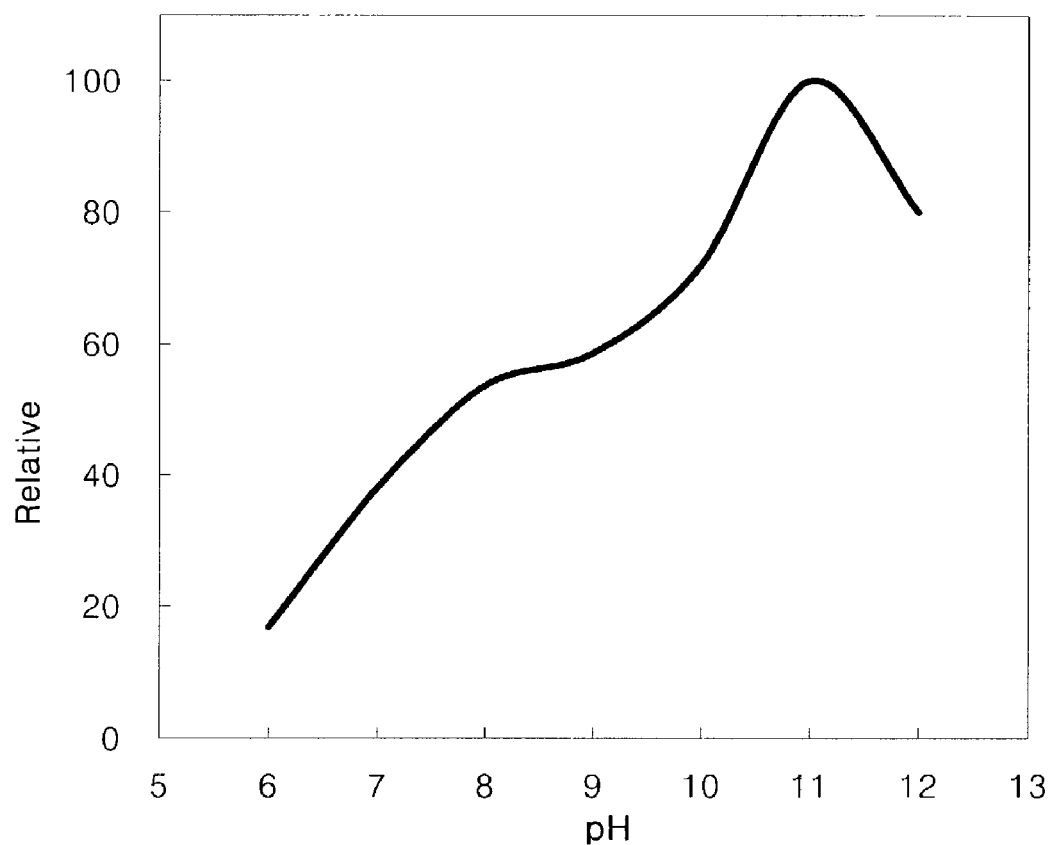
FIG. 1 depicts the pH effects upon the concentrated liquid enzyme (Vaps) according to the present invention.

In order to attain the objects mentioned above, the present invention provides a protease (Vaps) which is obtained from *Vibrio metschnikovii* RH variant strain, having a molecular weight in the range of 10,000~300,000, using azocasein as a substrate, and having a reaction temperature at the range of 40° C.~55° C. with the pH range of 10~12. Particularly, the protease obtained from *Vibrio metschnikovii* RH variant which is more than one strains selected among *Vibrio metschnikovii* KS1, *Vibrio metschnikovii* KS1 transformed with pDSBCm, *Vibrio metschnikovii* KS1 transformed with pSBCm and *Vibrio metschnikovii* RH530 N-4-8 strain, a mother strain of the above, is provided.

In addition, the present invention provides detergent compositions including the protease (Vaps), a stabilizer and a surfactant added in an acceptable amount for a detergent.

Hereinafter, the present invention will be described more clearly as follows.

In detail, it will be illustrated according to stages accomplished.

1. Experimental Strains

Strains used in the present invention will be described as follows. *Vibrio metschnikovii* KS1 was disclosed in PCT International Patent WO 00/61769 and has been deposited to the Corporation of Korean Culture Center of Microorganism, Seoul, Korea, an International Deposition Organization, as accession number KCCM-10141 on Dec. 5, 1998; *Vibrio metschnikovii* KS1 transformed with pSBCm has been deposited to the same organization as accession number KCCM-10142 on Dec. 5, 1998; and *Vibrio metschnikovii* KS1 transformed with pDSBCm is illustrated in PCT International Patent Application PCT/KR01/01232 and has been deposited to the same organization as accession number KCCM-10292 on Jul. 12, 2001.

The above strains are derived from *Vibrio metschnikovii* RH530 N-4-8 strain which is disclosed in Korean Patent Application No. 2000-41212 and has been deposited to Corporation Korean Culture Center of Microorganism, Seoul, Korea, an International Deposition Organization, as accession number KFCC-11030 on Feb. 23, 1998 and is a Gram negative, facultative anaerobe.

2. Cultivation of Strains

Although the strains mentioned above can grow in an aerobic condition, the supplying amount of oxygen is an important factor to affect the growth of strains and the productivity of the protease. Preferably, the culture temperature is at the range of 25° C.~35° C. and the optimal medium for the cell growth is LB medium (purchased from Difco company containing 0.5% of yeast extract, 1% of NaCl, and 1% of Tryptone) added with a sodium carbonate buffer (pH 10.5) adjusted to 50 mM finally. The optimal pH for the cell growth is in the range of 8.0~10 and the pH below 7 causes the cell growth retarded.

As a proper source of carbon, corn steep liquor (CSL) containing glucose is preferred in the range of 0.5~1%. The small amount of carbohydrates included in the nitrogen source such as soybean meal, wheat gluten meal and the like is also used as a proper carbon source.

Besides, as a nitrogen source, an organic nitrogen source such as soybean meal, wheat gluten meal, tuna extract, cotton seed flour, peanut meal, CSL, yeast extract, potato protein and the like, and an inorganic nitrogen source such as urea, ammonium sulfate and the like can be adopted in a proper amount. The organic nitrogen source is adjusted in the content to reach 3~4% (w/v), while the inorganic nitrogen source is adjusted to a small amount (under 0.2%).

3. Measurement of Enzymatic Activity

The enzymatic activity of the protease is measured by using the method disclosed in PCT International Patent Laid-open WO 00/61769. Concretely, 2 g of azocasein used as a substrate is dissolved in 100 ml of 50 mM sodium carbonate buffer(pH 10.5) and 1 ml of the above buffer solution is preheated at 40° C. for 10 minutes. Then, the diluted enzyme solution with the above buffer is mixed with the preheated substrate in a ratio of 1:1, and the mixture is reacted at 40° C. for 30 minutes. Thereafter, the reaction is stopped by adding 10% trichloroacetic acid into the whole reaction solution to be a ratio of 1:1. The above solution is centrifuged at 4° C. at 12,000 rpm for 10 minutes and 1 ml of the supernatant is adopted. Afterward, 1 ml of 0.5 N NaOH is added to the supernatant, and the absorbance are measured at O.D. 440 nm.

4. Separation, Purification and Concentration of the Enzyme

*Vibrio metschnikovii* KS1, a strain producing a protease, and *Vibrio metschnikovii* KS1 (pSBCm), a genetically modified strain are fermented in a culture media. Then, solid powder is eliminated through a sieve with about 100 mesh, and cells are removed by using the continuous centrifuge or the drum filtrator. 5~8% of ammonium sulfate is added to the above solution, and then melted and centrifuged in order to remove high molecular weight proteins and unnecessary contaminants. Thereafter, 50% of ammonium sulfate is poured, melted and filtered through the press filtrator so as to remove salts. The resulted enzyme solution obtained through the above procedure is ultrafiltrated again and finally the enzyme solution having the molecular weight in the range of 10,000~300,000 (hereinafter, referred to as "Vaps") is acquired.

The biochemical characteristics of the protease are examined as follows by using the refined and concentrated enzyme solution prepared above. Also, the stability is checked by adding the above enzyme solution to a heavy duty liquid detergent(HDL), and a cleaning power is confirmed in various kinds of surfactants and mixtures thereof.

5. Test of Washing Performance

In order to confirm effects of various surfactants and mixtures thereof on the enzyme, a washing power is examined in various conditions (according to the enzyme concentrations and the working concentration). The experimental conditions for the examination are demonstrated in Table 1 as follows. Each soiled swatch (purchased from EMPA company) is cut by 5 cm×5 cm in width and length. Then, the swatches are put into the Terg-O-tometer by five pieces per one section, and washed in accordance with the conditions referred in Table 1. Then, the washed cloths are spin-dried, rinsed 3 times, dried naturally and ironed so as to discriminate a difference in a washing power.

TABLE 1

| Item | Condition |
| --- | --- |
| Washing machine | Terg-O-tometer |
| Rotation speed | 100 rpm |
| Temperature | 40° C. |
| Washing time | 10 minutes |
| Washing pH | 10.5 |
|  | (50 mM sodium carbonate buffer) |
| Amount of surfactant used | 3,000 ppm |
| Amount of protease used | 9 PU/ml |
| Soiled fabrics | AS-10, EMPA-116, size: 5 cm × 5 cm |

EXAMPLES

The present invention will be clearly described in reference to the following examples hereinafter.

However, it will be appreciated that those skilled in the art, on consideration of this disclosure, may make modifications and improvements within the spirit and scope of the present invention.

Example 1

Cell Cultivation

One strain selected from strains producing alkaline protease mentioned above was inoculated to a seed culture media (as described in Table 2) and cultivated at 30° C. for 20 hours. Afterward, it was transferred to a 5 L—fermentor adjusting to 1% and cultivated again for about 40 hours. The compositions of the main culture medium and the seed culture medium were described in Table 2 and the working volume of liquid medium in 5 L—fermentor was adjusted to 3 L.

TABLE 2

| | Content in seed culture medium (%) | Content in main culture medium (%) |
|---|---|---|
| Soybean meal | 0.2 | 1.0 |
| Peanut powder | 0.1 | 0.5 |
| Potato protein | 0.3 | 0.5 |
| Corn steep liquor (CSL) | 0.2 | 1.0 |
| Yeast extract | 0.2 | 0.3 |
| NaCl | 0.5 | 0.5 |

The aeration in cultivating was adjusted to reach 0.5~0.7 vvm and the stirring speed was set to 500~600 rpm. The cultivated solution was centrifuged at 12,000 rpm for 5 minutes, and a supernatant was adopted to measure the final activity. As a result, the protease activity was estimated to be about 3,500 PU/ml.

Example 2

Collection, Purification and Concentration of Culture Broth

40 L of cultivated solution collected from 2nd fermentor with 30 L volume was filtered through 200 mesh sieve to eliminate large solid powders. Then, ammonium sulfate was added therein to be 5~8%, stirred for 30 minutes and centrifuged with a continuous centrifuge (at 4° C. and at 15,000 rpm) so as to remove cells and large molecules. As another method for removing cells and the like, a microfiltrator (1 $\mu$m, 0.45 $\mu$m) was utilized.

In order to increase the purity of the solution obtained through the above procedure, ammonium sulfate was treated again to be 50% and the resulted precipitate was dissolved in distilled water and recovered. Thereafter, the collected solution was ultrafiltrated to concentrate enzymes having the molecular weight in the range of 10,000~300,000, which were designated as "Vaps". Consequently, 150 ml of the enzyme solution having 200,000 PU/ml of the enzymatic activity was obtained.

Experimental Example 1

Investigation of Optimal pH and Optimal Temperature of the Protease

In order to elucidate biochemical characteristics of the protease, optimal pHs and temperatures for the protease activity were investigated. Buffers having respective pH range from 6 to 12 were prepared so as to measure an optimal pH for the activity of the protease. Precisely, disodium hydrogen phosphate ($Na_2HPO_4$)and sodium dihydrogen phosphate ($NaH_2PO_4$)were utilized to prepare buffers in pH 6, 7, 8, while boric acid and pottasium chloride (KCl) were exploited to prepare buffers in pH 9, 10. Disodium hydrogen phosphate ($Na_2HPO_4$) and sodium hydroxide (NaOH) were added to prepare buffers in pH 11, 12. In order to estimate the optimal pH for the enzymatic reaction, substrate was dissolved to buffers in each pH respectively and preheated at 40° C. for 10 minutes. Then, the enzyme was added to the above solution and reacted for 10 minutes before measuring the activity of the protease. Measurement of the optimal temperature for activity is performed under 25° C., 30° C., 40° C., 50° C., 55° C., 60° C. and 70° C. Vaps were added to azocasein substrate dissolved in 50 mM of sodium carbonate buffer (pH 10.5) and reacted for 10 minutes so as to measure the activity.

Figure 2:
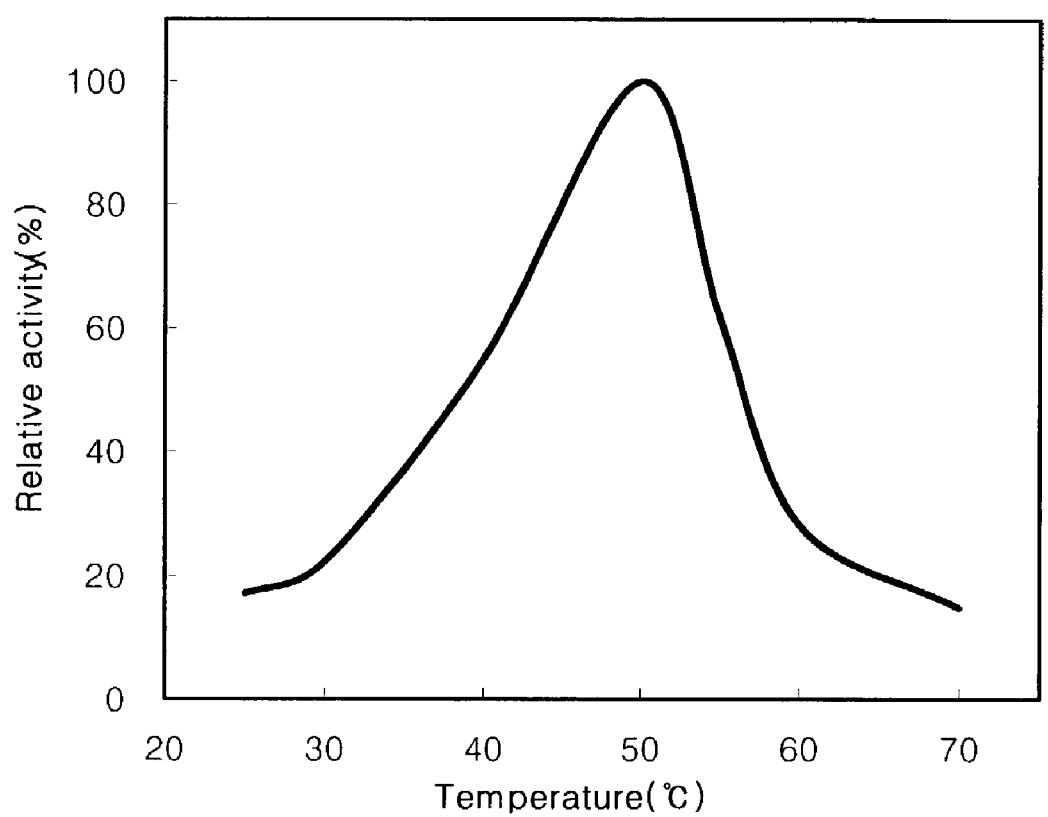
FIG. 2 depicts the temperature effects upon the concentrated liquid enzyme (Vaps) according to the present invention.

Consequently, optimal pHs were certified in the range of 10~11 (See FIG. 1, the relative activity was measured by considering the maximum activity as 100%) and the optimal reactive temperature was estimated in the range of 45~55° C. (See FIG. 2, the relative activity was measured by considering the maximum activity as 100%).

Experimental Example 2

Stability of Concentrated Enzyme (Vaps) in Heavy Duty Liquid Detergent (HDL)

Figure 3:
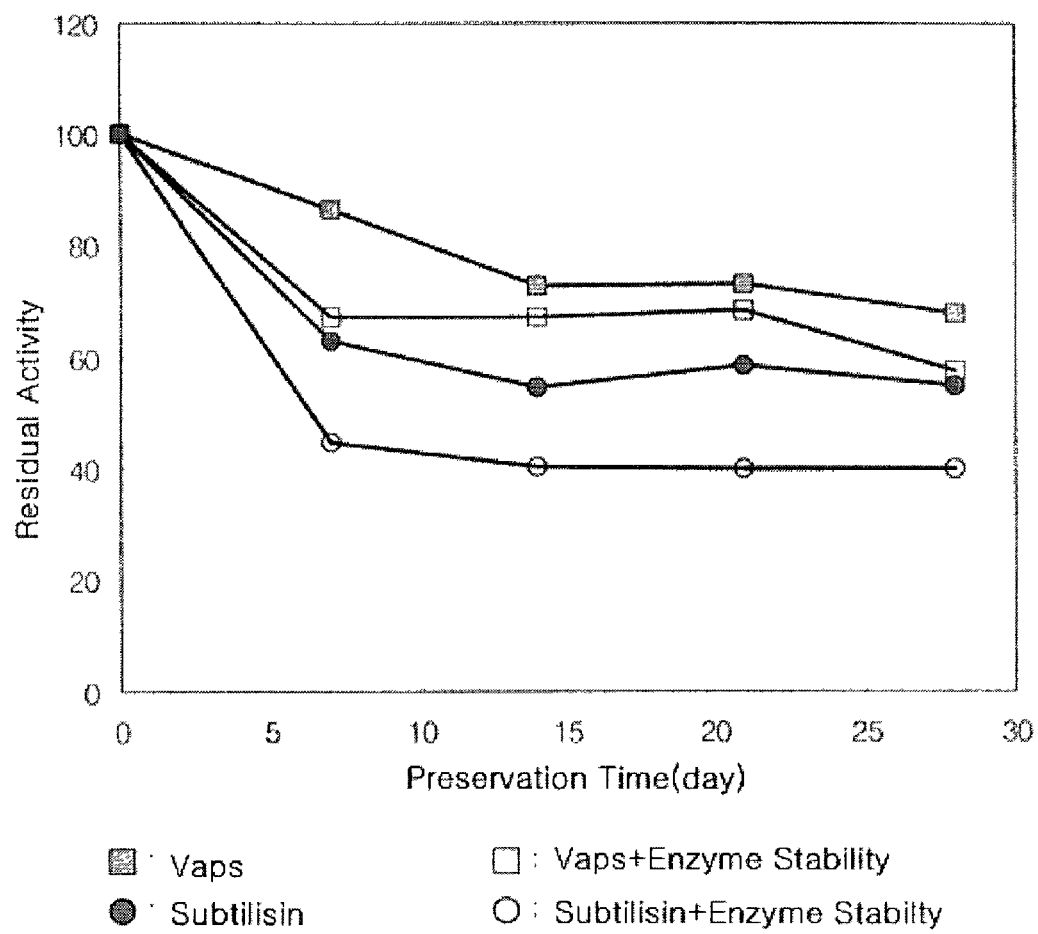
FIG. 3 depicts the preserving stability of the concentrated liquid enzyme (Vaps) of the present invention and subtilisin Carlsberg in a heavy duty liquid detergent.

In order to investigate the stability in a heavy duty liquid detergent, the experimental procedure was performed as follows by using the concentrated liquid enzyme prepared in Example 2. Materials of the highly concentrated detergent liquid were prescribed as depicted in Table 3. Precisely, linear alkylbenzene sulfonate (hereinafter, referred to as "LAS") of a negative ion, α-olefin sulfonate sodium salts (hereinafter, referred to as "AOS-Na") and sodium lauryl ether sulfonate (hereinafter, referred to as "SLES") were utilized as a major surfactant. On the other hand, glycerol, ethylene glycol, calcium chloride dihydrate ($CaCl_2.2H_2O$), sodium borate, and sodium formate were exploited as an enzyme stabilizer. As a comparative enzyme for contrasting the enzyme stability, subtilisin Carlsberg was used and preserved in an incubator at 40° C. for 28 days, and its residual activity was measured once a week (See FIG. 3). As a result, in case of adding an enzyme stabilizer, Vaps was more stable than subtilisin Carlsberg by about 5~10%, and Vaps also showed higher stability in a state without an enzyme stabilizer.

TABLE 3

Heavy duty liquid detergent (HDL)

| Ingredients | Content | |
|---|---|---|
| Linear alkylbenzene sulfonate (LAS) | 11.5% | Negative |
| α-olefin sulfonate sodium salt (AOS-Na) | 7.0% | Ion surfactant |
| sodium lauryl ether sulfate (SLES) | 11.3% | |
| Glycerol | 17.7% | Enzyme |
| Ethylene glycol | 8.0% | stabilizer |
| Calcium chloride dihydrate | 4.4 mM | |
| Sodium borate | 88.8 mM | |
| Sodium formate | 44.4 mM | |
| Nitrilotriacetic acid sodium salt | 0.23% | |
| Vaps | 0.5% | protease |
| Subtilisin Carlsberg | 0.5% | |
| Deionized water | to 100.0% | |

Experimental Example 3

Effects of Various Surfactants on Washing Power of the Protease

Effects of various surfactants added in a separate mode or in a complex mode on a washing power of the protease (Vaps) prepared in Example 2 were certified. As a surfactant, LAS, AOS, SLES which are anionic and polyoxyethylene (POE) (7eo) which is non-ionic were utilized. The cleaning power was measured by using 2 kinds of soiled swatch under conditions as follows.

TABLE 4

Cleaning power of enzyme according to concentrations

| | Final concentration of detergent | 1M sodium carbonate buffer (pH 10.5) | Enzyme solution (A, B) | Calcium carbonate | Deionized water |
| --- | --- | --- | --- | --- | --- |
| Batch 1 | 4,000 ppm | 50 mM | 0.000% | 50 ppm | Final 1l |
| Batch 2 | 4,000 ppm | 50 mM | 0.001% | 50 ppm | Final 1l |
| Batch 3 | 4,000 ppm | 50 mM | 0.002% | 50 ppm | Final 1l |
| Batch 4 | 4,000 ppm | 50 mM | 0.003% | 50 ppm | Final 1l |
| Batch 5 | 4,000 ppm | 50 mM | 0.004% | 50 ppm | Final 1l | temperature 40° C., artificial soiled swatch (EMPA 116, AS-10)

TABLE 5

Washing power of enzyme according to temperatures

| | Final concentration of detergent | 1M sodium carbonate buffer (pH 10.5) | Acting temperature (° C.) | Calcium carbonate | Deionized water |
| --- | --- | --- | --- | --- | --- |
| Batch 1 | 4,000 ppm | 50 mM | 20 | 50 ppm | Final 1l |
| Batch 2 | 4,000 ppm | 50 mM | 30 | 50 ppm | Final 1l |
| Batch 3 | 4,000 ppm | 50 mM | 40 | 50 ppm | Final 1l |

Enzyme (A, B) concentration 0.004%, artificial soiled swatch (EMPA 116, AS-10)

Figure 4:
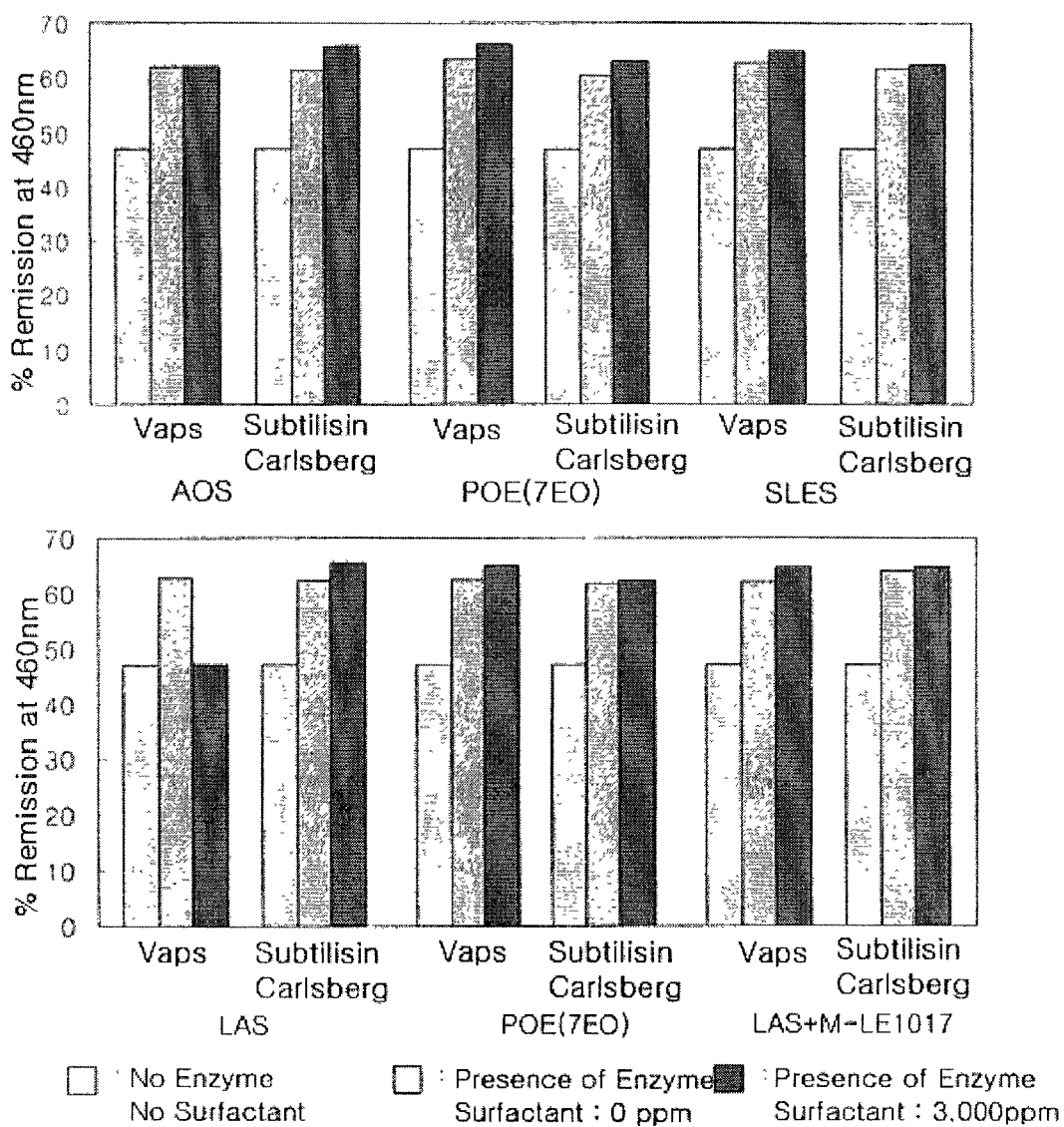
FIG. 4 depicts the effects of various surfactants upon washing power of the protease according to the present invention.

As a result, the washing power of Vaps was revealed very poor in the presence of linear alkylbenzene sulfonate (LAS), but it was recoverd completely by mixing linear alkylbenzene sulfonate with non-ionic surfactant, POE(7eo) in a ratio of 1:1. Especially, Vaps was superior to subtilisin Carlsberg in the washing power in the presence of non-ionic surfactant and SLES (See FIG. 4).

Figure 5:
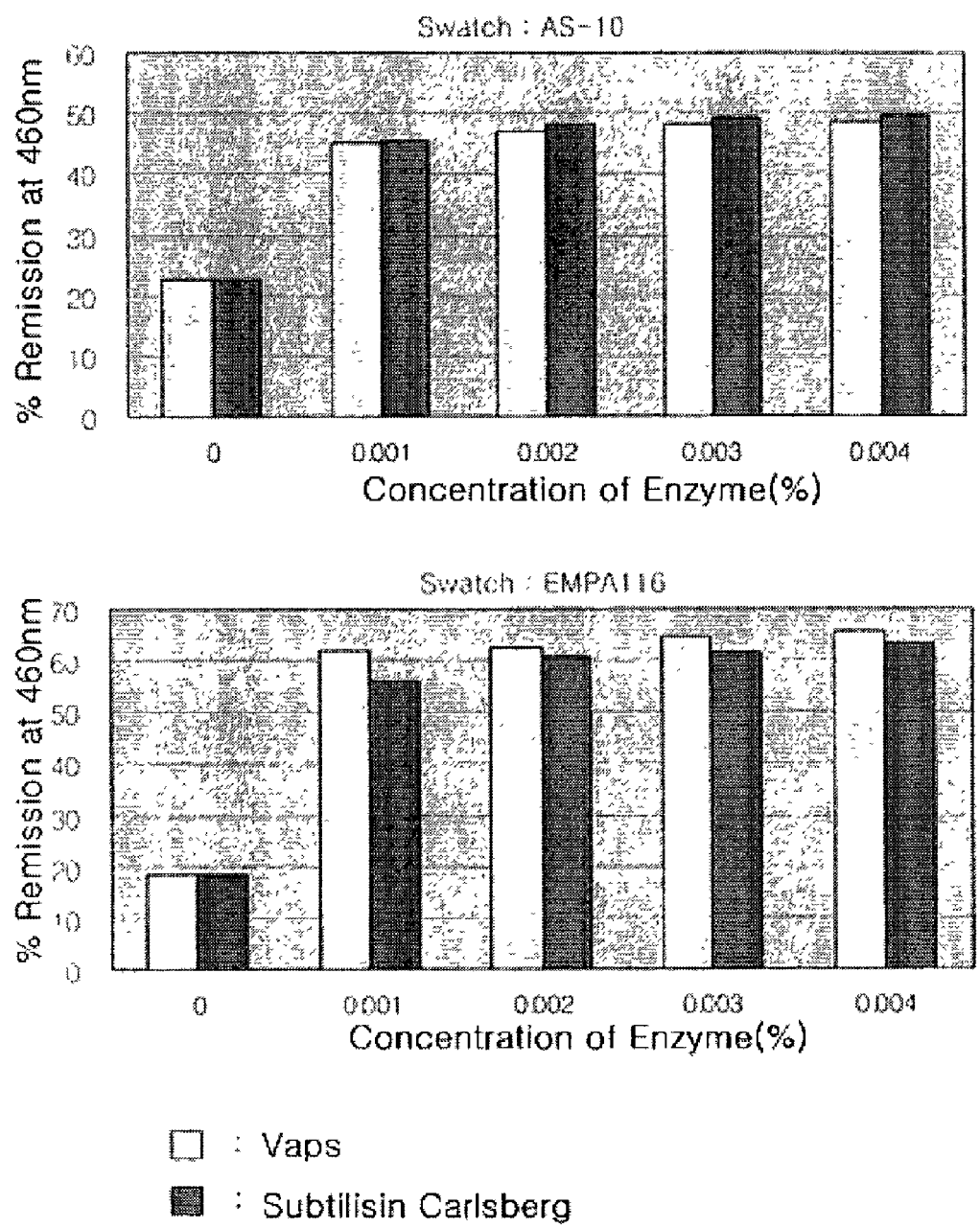
FIG. 5 depicts the examination of washing power of the protease of the present invention in accordance with the concentrations of the protease.

Besides, in order to investigate effects of various surfactants in mixtures upon the washing power of the enzyme, the detergent in which LAS, SLES, AOS, and POE(7eo) were mixed in a ratio of 1:1:1:1 (finally up to 4,000 ppm) as the compositions demonstrated in Table 4 was utilized. As a result, Vaps maintained a relatively superior washing power to subtilisin Carlsberg in case of using the AS-10, while showed a similar washing power to subtilisin Carlsberg in case of using the EMPA-116 as an soiled fabric (See FIG. 5).

Figure 6:
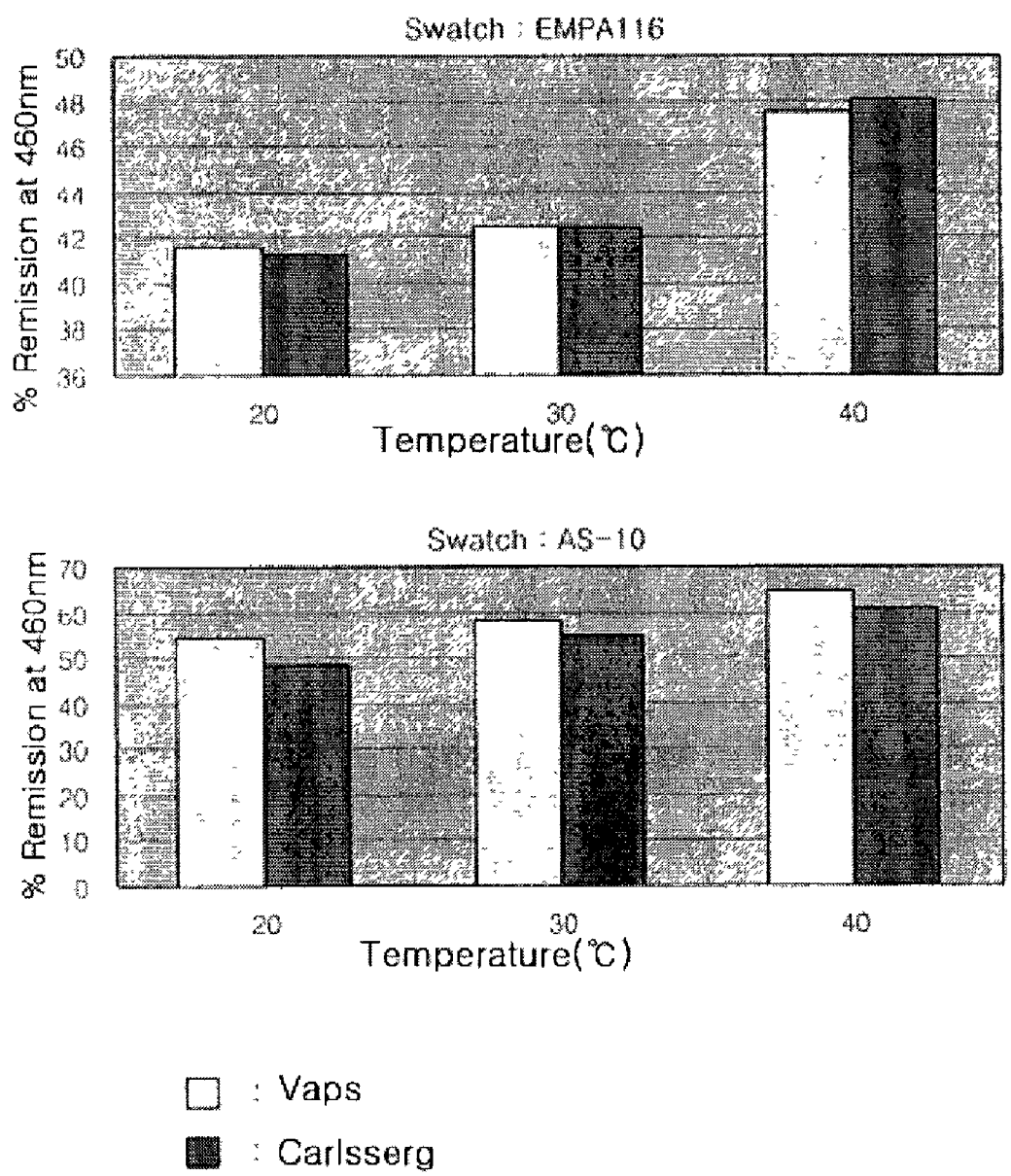
FIG. 6 depicts the examination of washing power of the protease of the present invention in accordance with the temperatures.

In addition, when the washing power against temperatures was tested under conditions as described in the above Table 5, Vaps was verified to exceed subtilisin Carlsberg in washing power by around 6% at a low temperature (20° c.) and to be almost equal to subtilisin Carlsberg at a high temperature (40° C.) (See FIG. 6).

Furthermore, when the difference of the cleaning power against enzyme concentrations, it was confirmed that the higher the enzyme concentrations is, the higher the washing power is improved. Vaps was identified to have more outstanding cleaning power in the AS-10 soiled fabric even at a lower concentration (0.001%) than subtilisin Carlsberg by about 6%.

INDUSTRIAL APPLICABILITY

As demonstrated and confirmed above, the present invention provides a protease improving the washing power and the enzyme stability highly and detergent compositions containing the protease. Therefore, the protease and detergent compositions comprising the same can be applied usefully and widely.

What is claimed is:

1. A protease obtained from *Vibrio metschnikovii* RH variant having a molecular weight in the range of 10,000–300,000, utilizing azocasein as a substrate, and having 10–12 pH at 40° C.–55° C.

2. The protease according to claim 1, wherein *Vibrio metschnikovii* RH variant strains is obtained from more than one strains selected from the group consisting of *Vibrio metschnikovii* KS1, *Vibrio metschnikovii* KS1 transformed with pDSBCm, *Vibrio metschnikovii* KS1 transformed with pSBCm and the mother strain, *Vibrio metschinikovii* RH530 N-4-8.

3. A detergent composition prepared by adding a stabilizer or a surfactant in an acceptable amount for a detergent to said protease (Vepe) of claim 1.

4. The detergent composition according to claim 3, wherein said surfactant is more than one selected from the group consisting of linear alkylbenzene sulfonate, .alpha.-olefin sulfonate sodium salt (AQS) and sodium lauryl ether sulfate.

5. The detergent composition according to claim 3, wherein said stabilizer is selected from the group consisting of glycerol, ethylene glycol, calcium chloride dihydrate, sodium borate and sodium formate.

* * * * *